US00PP10559P

United States Patent [19]

Holtkamp, Sr.

[11] Patent Number: Plant 10,559

[45] Date of Patent: Aug. 18, 1998

[54] AFRICAN VIOLET PLANT NAMED LEONARDO DA VINCI

[75] Inventor: Reinhold Holtkamp, Sr., Ress-Haffen, Germany

[73] Assignee: International Plant Breeding A.G., Bern, Switzerland

[21] Appl. No.: 798,298

[22] Filed: Feb. 7, 1997

[51] Int. Cl.[6] ..... A01H 5/00

[52] U.S. Cl. ..... Plt./69.1

[58] Field of Search ..... Plt./69.1

*Primary Examiner*—James R. Feyrer
*Assistant Examiner*—Melissa L. Kimball
*Attorney, Agent, or Firm*—Foley & Lardner

[57] ABSTRACT

A new and distinct cultivar of African violet named Leonardo da Vinci, as described and illustrated, and particularly characterized by its single violet-shaped multi-colored flowers which have a white center and some white edges and an intensive purplish red patch on each of the three large petals (occasionnally on the two small petals also) that fades out to a lighter purplish red color; strong, upright flower stems that curve slightly toward the center to form a compact bouquet above the leaves; medium green, oval to heart-shaped leaves; profuse flowering; vigorous and compact growth habit; flowering 9–10 weeks after potting, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Leonardo da Vinci.

The new cultivar was referred to during the breeding and selection process by the designation 1062/16 and is a product of a planned breeding program. The new cultivar was originated from a cross made by me in the controlled breeding program in Haffen, Federal Republic of Germany. The female, or seed parent was a cultivar designated 760. The male, or pollen parent was a cultivar designated 1062.

Leonardo da Vinci was discovered and selected by me as a flowering plant within the progeny of the stated cross in a controlled environment in Haffen, West Germany. A sexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Leonardo da Vinci has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Leonardo da Vinci, which in combination distinguish this African violet as a new and distinct cultivar:

1) Strong, upright flower stems curving slightly toward the center.

2) Single violet-shaped multi-colored flowers with white centers and edges and an intensive purplish red patch on each of the three large petals (occasionnally on the two small petals also) that fades out to a lighter purplish red color.

3) Profuse flowering.

4) Each plant carries 6–8 and more upright flower stems each of which carries 10–12 and more flowers.

5) Long lasting, non-dropping flowers.

6) Vigorous and compact grower.

7) Plant saleable 9–10 weeks after potting.

8) Seed capsules push slightly through.

9) Medium green, oval to heart-shaped leaves.

10) After maturity the flowers dry off, and remain on the peduncle without becoming infected by botrytis.

The new cultivar is most similar to Van Gogh, for which a U.S. plant patent is also in the process of being applied for. Both cultivars have a similar unique bi-colored designs on the blossoms with white and another color. However, Van Gogh has a large white center with evenly colored dark lilac petals whereas Leonardo da Vinci has white in the center and on some of the petal edges and an intensive purplish red patch on each of the three large petals (occasionnally on the two small petals also) which fades out to a lighter purplish red color.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 12 p.m. in Nashville, Tenn.

Botanical classification: *Saintpaulia ionantha*, Ramat., c.v. Leonardo da Vinci.

Parentage:

*Male parent.*—1062.

*Female parent.*—760.

Propagation: The new cultivar holds its distinguishing characteristics through successive propagations by leaf cuttings.

Plant: From 8 cm to 11 cm tall when grown in pots, and 24–28 cm in diameter when fully grown.

*Leaves.*—General form: Oval to heart-shaped. Diameter: 60–70 mm wide and 70–80 mm long. Texture: Velvety. Aspect: Slightly serrated, hairy, slightly shiny. Veins: Upperside: visible; underside: well pronounced, light green, shiny. Color (upperside): Yellow-green group147 A. Color (underside): Yellow-green group 148D Petiole: Strong, light green, hairy.

*Flowers*—Buds: Bell-shaped, greenish and purplish red touch, 5–7 mm just before opening. Sepals: Five (5). Color: Purplish brown. Calyx: Shape: Funnel-shaped. Aspect: Spear-shaped, hairy. Peduncle: Character: Strong upright, hairy. Color: Green, occasionally brownish touch.

*Individual flowers.*—Size: 35–40 mm. Shape: Single violet-shaped with slightly wavy petal tips. Color (upperside): The center and some edges are white with a patch on each of the three large petals that is between Purple violet group 80 A and red-purple group 74 A. The patches fade out to purple violet group 80 B to C. On the two small petals the color ranges from purple violet group 80 B to C or almost white. Under cooler temperatures and more intensive lighting, the purplish red tends to intensify. Color (underside): Centers and some edges are white with petals being violet group 80 B to C. Borne: each flower stem carries 10–12 and more flowers on strong, upright peduncles that are free standing above the leaves, thereby forming a compact bouquet. Flowering habit: Flowers 9–10 weeks after potting.

*Reproductive organs.*— Stamens: Two (2). Anthers: 2 composed of 4 anther cells, seed capsules push slightly through. Filaments: Yellowish white, 3–4 mm long. Pollen Color: Yellow Group 7 A. Styles: 7–8 mm long, purplish red, base of ovary light green and hairy.

*Roots.*—Normally developed, white when young, turning slightly brownish when older.

Disease resistance: Up to date, Leonardo da Vinci has shown very good resistance to all major violet diseases.

General Observations

Leonardo da Vinci is an attractive cultivar due to its unique multi-colored white and intensive purplish red flowers. The center and some of the edges are white contrasting nicely with the intensive purplish red patch on each of the three large petals. The purplish red fades away to a lighter purplish red and is also less intensive on the two small petals. The amount of purplish red spread may vary just slightly from one blossom to another. A tight bouquet of flowers free standing above the leaves develops 9–10 weeks after potting. Each of the 6–8 and more strong flower stems carries 10–12 and more single violet-shaped flowers with slightly wavy petal tips. Medium green, oval to heart-shaped leaves surround the flower bouquet. The flowers are long-lasting and non-dropping and the seed capsules push slightly through.

I claim:

1. A new and distinct cultivar of African violet plant named Leonardo da Vinci, as described and illustrated, and particularly characterized by its single violet-shaped multi-colored flowers which have a white center and some white edges and an intensive purplish red patch on each of the three large petals (occasionnally on the two small petals also) that fades out to a lighter purplish red color; strong, upright flower stems that curve slightly toward the center to form a compact bouquet above the leaves; medium green, oval to heart-shaped leaves; profuse flowering; vigorous and compact growth habit; flowering 9–10 weeks after potting, and by its long lasting and non-dropping flowers.

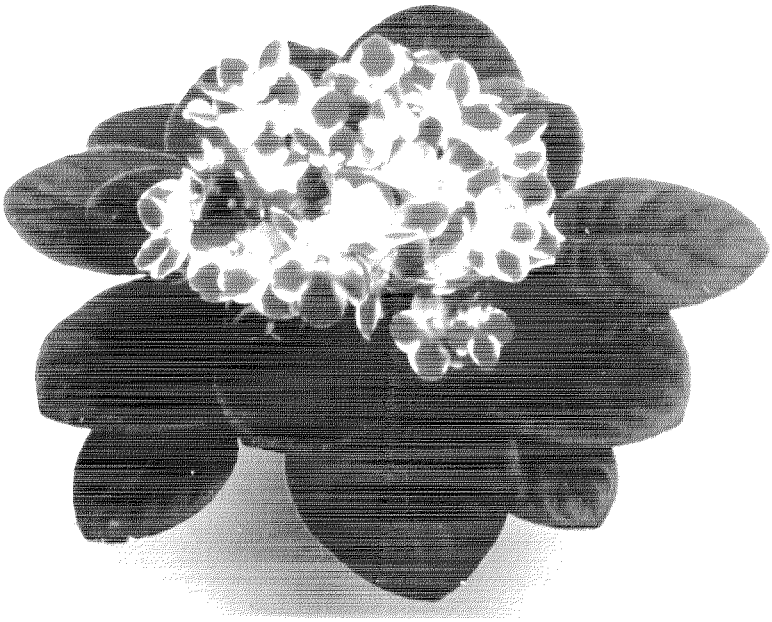

* * * * *